United States Patent [19]
Fagan

[11] Patent Number: 5,382,719
[45] Date of Patent: Jan. 17, 1995

[54] FLUOROALKYLATED FULLERENE COMPOUNDS

[75] Inventor: Paul J. Fagan, Wilmington, Del.

[73] Assignee: E. I. Du Pont de Nemours and Company, Wilmington, Del.

[21] Appl. No.: 230,027

[22] Filed: Apr. 19, 1994

Related U.S. Application Data

[62] Division of Ser. No. 21,395, Feb. 23, 1993.

[51] Int. Cl.$^6$ .................... C07C 17/24; C07C 17/28; C07C 17/32; C07C 22/08
[52] U.S. Cl. .................................... 570/144; 570/129
[58] Field of Search ........................................... 570/144

[56] References Cited

U.S. PATENT DOCUMENTS 3,281,426 10/1966 Tiers ..................... 570/144

FOREIGN PATENT DOCUMENTS 2-62832 3/1990 Japan .

OTHER PUBLICATIONS

R. E. Haulfer et al, *J. Phys. Chem.*, vol. 94, 8634–8636 (1990).
P. M. Allemand et al, *J. Am. Chem. Soc.*, vol. 113, 1050–1051 (1991).
F. Diederich et al, *Science*, vol. 252, 548–551 (1991).
K. Kikuchi et al, *Chem. Phys. Lett.*, vol. 188, No. 3, 4, 177–180 (1992).
C. Smart et al, *Chem. Phys. Lett.*, vol. 188, No. 3, 4, 171–176 (1992).
H. Shinohara et al, *J. Phys. Chem.*, 95, 8449–8451 (1991).
P. J. Krusic et al, *J. Am. Chem. Soc.*, vol. 113(16), 6274–6275 (1991).
R. Taylor et al, *Nature*, vol. 355, 27–28 (1992).
P. E. Ross, *Scientific American*, 114–116 (Jan. 1991).
R. F. Curl et al, *Scientific American*, 54–63 (Oct. 1991).
J. R. Morton et al, *J. Chem. Soc. Perkin Trans.* 2, 1425–1429 (1992).
J. R. Morton et al, *J. Phys. Chem.*, 96(9), 3576–3578 (1992).
P. J. Krusic et al, *Science*, 254, 1183–1185 (1991).
P. J. Fagan et al, *J. Am. Chem. Soc.*, 114(24), 9697–9699 (1992).
J. R. Morton et al, *J. Amer. Chem. Soc.*, 114, 5454–5455 (1992).
J. W. Bausch et al, *J. Am. Chem. Soc.*, 113, 3205–3206 (1991).
D. Schroder et al, *Int. J. Mass Spectrum. and Ion Processes*, 116, R13–R21 (1992).
C. L. McEwen et al, *J. Am. Chem. Soc.*, 114, 4412–4414 (1992).
W. Kratschmer et al, *Nature*, 347–354 (1990).
R. M. Baum, *C&EN*, 22–25 (Oct. 1990).
M. H. Habibi et al, *J. Fluorine Chem.*, vol. 53, 53–60 (1991).
R. N. Haszeldine et al, *J. Chem. Soc.*, 3483–3490 (1952).
Z. Chengxue et al, *J. Org. Chem.*, 47, 2009–2013 (1982).
S. Iijima, *Nature*, vol. 354, 56–58 (1991).
M. H. Habibi et al, J. Fluorine Chem., vol. 55, 53–60 (1991).

Primary Examiner—Joseph E. Evans

[57] ABSTRACT

This invention provides a mixture of fluoroalkylated fullerene compounds, preferably perfluoroalkylated fullerene compounds, comprising the formula, $(C_{60+2n})R^1_m R^2_b Z_y$, wherein $R^1$ is a branched or straight chain hydrocarbon or aromatic hydrocarbon of from 1 to about 100 carbon atoms; $R^2$ is a branched or straight chain fluoroalkyl group of from 1 to about 100 carbon atoms; Z is one or more selected from H, F and Cl; n is an integer from 0 to about 470; m is an integer from 0 to about $24+n$; b is an integer from 1 to about $24+n$; and y is an integer from 0 to about $35+n$.

6 Claims, No Drawings

FLUOROALKYLATED FULLERENE COMPOUNDS

This is a division of application Ser. No. 08/021,395, filed Feb. 23, 1993.

This invention relates to mixtures of fluoroalkylated fullerene compounds and their preparation.

Recent success in synthesizing macroscopic quantities of carbon clusters such as $C_{60}$ and $C_{70}$ (known as fullerenes), by W. Kratschmer et al., Nature, 347–354 (1990), has opened the door to the study of this new class of organic compounds. Kratschmer et al. describe the fullerene molecule $C_{60}$ (also known as buckminsterfullerene) as a centrosymmetric truncated icosahedron. Pure solid buckminsterfullerene consists of a somewhat disordered face centered cubic or hexagonal close packing of the centrosymmetric molecules. Isolation and characterization of higher fullerenes, specifically $C_{76}$, $C_{84}$, $C_{90}$, and $C_{94}$, have been disclosed by Francois Diederich et al., Science, Vol. 252, pages 548–551 (1991). Mixtures of giant fullerene molecules, e.g., $C_{540}$, have been discussed by C. Smart et al., Chem. Phys. Lett., Vol. 188, No. 3,4, pages 171–176 (Jan. 10, 1992).

Electrochemical studies on fullerenes, e.g., R. E. Haufler et al., J. Phys. Chem., Vol. 94, pages 8634–8636 (1990) and P. M. Allemand et al., J. Am. Chem. Soc., Vol. 113, pages 1050–1051 (1991), indicate that fullerenes per se are excellent electron acceptors. Organic radicals have been shown to readily add to the double bonds of $C_{60}$ to afford complex mixtures of adducts, $R_nC_{60}$, e.g., J. R. Morton et al., J. Chem. Soc. Perkin Trans. 2, pp. 1425–1429 (1992); J. R. Morton et al., J. Amer. Chem. Soc., 114, pp. 5454–5455 (1992); J. R. Morton et al., J. of Phys. Chem., 96(9), pp. 3576–3578 (1992); P. J. Krusic et al., J. Am. Chem. Soc., Vol. 113(16), pp. 6274–6275 (1991); P. J. Krusic et al., Science, 254, pp. 1183–1185 (1991). In J. Am. Chem. Soc., 113, pp. 3205–3206 (1991), J. W. Bausch et al. describe the preparation of polymethylated fullerenes.

Early in the speculations about applications of fullerenes, the possibility of fluorine-coated $C_{60}$ was raised, e.g., in Scientific American, pp. 114–116, January 1991 and Scientific American, pp. 54–63, October 1991. However, initial attempts by others to produce a "spherical Teflon®" led to materials which were incompletely fluorinated and reacted with moisture, see Nature, Vol. 355, pp. 27–28, January 1992.

An object of this invention is to provide a mixture comprising fluoroalkylated fullerene compounds, preferably perfluoroalkylated fullerene compounds.

SUMMARY OF THE INVENTION

This invention comprises a mixture of fluoroalkylated fullerene compounds comprising formula (I)

$$(C_{60+2n})R^1{}_mR^2{}_bZ_y \quad (I)$$

wherein $R^1$ is a branched or straight chain hydrocarbon or aromatic hydrocarbon of from 1 to about 100 carbon atoms;

$R^2$ is a branched or straight chain fluoroalkyl group of from 1 to about 100 carbon atoms;

Z is independently one or more selected from H, F and Cl;

n is an integer from 0 to about 470;

m is an integer from 0 to about 24+n;

b is an integer from 1 to about 24+n; and y is an integer from 0 to about 35+n.

This invention also comprises a photolysis process for the preparation of a mixture of fluoroalkylated fullerene compounds said process comprising photolysing a solution or slurry of fullerene compounds of formula II $$(C_{60+2n})R^1{}_mZ_y \quad (II)$$

wherein n is an integer from 0 to about 470;

$R^1$ is a branched or straight chain hydrocarbon or aromatic hydrocarbon of from 1 to about 100 carbon atoms;

m is an integer from 0 to about 24+n;

Z is independently one or more selected from H, F and Cl;

y is an integer from 0 to about 35+n, with compounds of formula III or formula IV $$R^2X_q \quad (III)$$

$$R^2{}_bCO_2-O_2CR^2{}_b \quad (IV)$$

wherein $R^2$ is a branched or straight chain fluoroalkyl group of from 1 to about 100 carbon atoms;

X is independently Cl, Br or I;

b is an integer from 1 to about 24; and q is an integer of 1 or 2, to yield a mixture of fluoroalkylated fullerene compounds comprising formula (I), $(C_{60+2n})R^1{}_mR^2{}_bZ_y$, as defined above wherein b is an integer from 1 to about 24+n.

This invention also comprises a thermolysis process for the preparation of a mixture of fluoroalkylated fullerene compounds said process comprising: heating fullerene compounds of formula II, $(C_{60+2n})R^1{}_mZ_y$, as defined above, with compounds of formula III, $R^2X_q$, as defined above, at a temperature of from about 160° to about 300° C., under a pressure of 0 to about $4.1 \times 10^5$ Pascals (0 to about 60 psi) of an inert gas atmosphere, for about 1 hour to about 96 hours; to yield a mixture of fluoroalkylated fullerene compounds comprising formula (I), $(C_{60+2n})R^1{}_mR^2{}_bZ_y$, as described above wherein b is an integer from 1 to about 24+n.

The invention also comprises a thermolysis process for the preparation of a mixture of fluoroalkylated fullerene compounds, said process comprising: heating fullerene compounds of formula II, $(C_{60+2n})R^1{}_mZ_y$, as defined above, with compounds of formula IV, $R^2{}_bCO_2-O_2CR^2{}_b$, as defined above, at a temperature of from about 25° C. to about 100° C. in the presence of a halocarbon solvent, under a pressure of 0 to about $4.1 \times 10^5$ Pascals (0 to about 60 psi) of inert gas atmosphere, for about 1 hour to about 96 hours; to yield a mixture of fluoroalkylated fullerene compounds of formula I, $(C_{60+2n})R^1{}_mR^2{}_bZ_y$, as defined above wherein b is an integer from 1 to about 24+n.

In the mixture of fluoroalkylated fullerene compounds of formula I, $(C_{60+2n})R^1{}_mR^2{}_bZ_y$, $R^1$, $R^2$ and Z are each independently attached directly to the $C_{60+2n}$ molecules.

The description of the claimed compounds as a "mixture" indicates that due to practical considerations and the present state of the art the starting fullerene compounds will most likely be comprised of a mixture of $C_{60}$ molecules together with $C_{60+2n}$ molecules, wherein n may be 0 to about 470, most likely n=1 to 5. Starting fullerene compounds of the invention substituted with $R^1$ hydrocarbon and/or Z can also be comprised of a mixture. Not only can the fullerene compounds, to which the $R^1$ hydrocarbon and/or Z molecules are attached, be a mixture of $C_{60}$ together with $C_{60+2n}$ molecules, but the individual $R^1$ hydrocarbons and/or Z molecules attached to them may vary from compound to compound within the mixture in both the number of substituents per fullerene compound and structure. For example, a starting mixture may be comprised of fullerene compounds such as, $C_{60}(R^1)_4H_4$ together with $C_{60}(R^{1*})_6(R^{1**})_6H_{12}$ and $C_{70}(R^1)_2$, wherein $R^{1*}$ and $R^{1**}$ are two different $R^1$ hydrocarbons. Thus, the reaction of these mixtures of fullerene molecules with the fluoroalkyl reactants of the invention yields a mixture of product fullerene molecules. Further, it is known that the fluoroalkyl reactant molecules may add nonuniformly to the surface of each of the fullerene molecules within each reaction mixture. Because of this fact also, therefore, the claimed fluoroalkylated fullerenes of the invention are most properly described herein as "mixtures ."

DETAILED DESCRIPTION OF THE INVENTION

This invention provides a mixture of fluoroalkylated fullerene compounds, preferably perfluoroalkylated fullerene compounds, comprising formula (I)

$(C_{60+2n}) R^1_m R^2_b Z_y$  (I)

wherein $R^1$ is a branched or straight chain hydrocarbon or aromatic hydrocarbon containing from 1 to about 100 carbon atoms. $R^2$ is a branched or straight chain fluoroalkyl group, preferably perfluoroalkyl, of from 1 to about 100 carbon atoms, preferably from 1 to about 50 carbon atoms, and most preferably from 1 to about 8 carbon atoms. Z is independently one or more selected from H, F and Cl, preferably H. n is an integer from 0 to about 470, preferably an integer from 0 to about 200 and, most preferably, an integer from 0 to about 5. When n=0, m is an integer from 0 to about 24, preferably from 0 to about 12, and most preferably from 0 to about 6; b is an integer from 1 to about 24, preferably an integer from 5 to about 17 and, most preferably, an integer from 7 to about 16; and y is an integer from 0 to about 35, preferably an integer from 0 to about 3. For n>0, m, b and y are correspondingly larger, for example, for n=5, m=0 to about 29, e.g., 0 to about (24+n); b=1 to about 29, e.g., 1 to about (24+n); and y=0 to about 39, e.g., 0 to about (35+n). For n=10, m=0 to about 34, e.g., 0 to about (24+n); b=1 to about 34, e.g., 1 to about (24+n); and y=0 to about 45, e.g., 0 to about (35+n).

It is anticipated that carbon nanotubules as first prepared by Iijima (S. Iijima, Nature, Vol. 354, pp. 56-58 (1991) will also react and be fluoroalkylated by the procedures described in this invention. This is based on the structural similarity of the endcaps of these tubes to fullerenes and the curved nature of the tubule surfaces which is characteristic of fullerenes such as $C_{60}$ and $C_{70}$.

A variety of processes are known in the art for fluoroalkylating traditional organic compounds. However, because of the unique structure and chemistry of fullerenes, the degree of uncertainty of successful fluoroalkylation was high. In accordance with this invention, it has been found that both a photolysis and a thermolysis method are satisfactory.

Both preparative processes may utilize fullerene compounds of formula II, $(C_{60+2n})R^1_m Z_y$, which may include pure unsubstituted fullerenes, or fullerenes substituted with $R^1$ hydrocarbon and/or Z (H, F and Cl) or mixtures thereof. These molecules are reacted with fluoroalkyls of formula III, $R^2 X_q$, or mixtures thereof, preferably with perfluoroalkyliodide(s), e.g., $CF_3(CF_2)_5I$; or perfluoroalkyldiiodide(s), e.g., $I(CF_2)_4I$; or with fluoroalkyl compounds of formula IV, $R^2_bCO_2-O_2CR^2_b$, or mixtures thereof, such as perfluoroalkanoylperoxides, e.g., $CF_3CF_2CO_2-O_2CCF_2CF_3$; as the starting reagents. The above fluoroalkyls are common commercially available materials. The fullerene compounds of formula II, $(C_{60+2n})R^1_m Z_y$, can be prepared by a variety of methods known in the art, for example by the methods of Kratschmer et al., Diederich et al. and by Smart et al., all of which are cited above. Mixtures of unsubstituted fullerenes can be prepared by Kratschmer et al., Diederich et al., and by Smart et al. (cited above) or are available commercially from Texas Fullerenes Corporation, 2415 Shakespeare Suite 5, Houston, Tex. 77030-1038.

The photolysis process for the preparation of traditional fluoroalkylated organic compounds is generally known in the art, for example M. H. Habibi; T. E. Mallouk, J. Fluorine Chem., Vol. 53, pp. 53-60 (1991). Utilizing the photolysis alkylation process to prepare the mixtures of fluoroalkylated fullerene compounds in accordance with this invention involves photolysing with a mercury lamp or other source of ultraviolet and visible light a solution or slurry of fullerene compounds of formula II, $(C_{60+2n})R^1_m Z_y$, with compounds of formula III, $R^2 X_q$, such as pure perfluoroalkylhalide or a mixture of perfluoroalkylhalides, or with compounds of formula IV, $R^2_bCO_2-O_2CR^2_b$, with or without an organic or halocarbon solvent from about 10 minutes to about 48 hours, usually about 10 minutes to about two hours, and preferably under an inert gas atmosphere such as dinitrogen in the absence of oxygen. Examples of suitable organic or halocarbon solvents include hexafluorobenzene; 1,2,4-trichlorobenzene; Freon® 113 and benzene.

The thermolysis process for the preparation of traditional fluoroalkylated organic compounds is generally known in the art, for example R. N. Haszeldine; K. Leedham, J. Chem. Soc., p. 3483 (1952). Utilizing the thermolysis fluoroalkylation process to prepare the mixtures of fluoroalkylated fullerene compounds in accordance with this invention involves heating fullerene compounds of formula II, $(C_{60+2n})R^1_m Z_y$, with compounds of formula III, $R^2 X_q$, such as pure fluoroalkylhalide or a mixture of fluoroalkylhalides, preferably perfluoroalkyliodides or perfluoroalkyldiiodides, from about 160° to about 300° C., preferably from about 180° to about 220° C., and most preferably from about 180° to about 200° C. without, or preferably with, an organic or halocarbon solvent, such as 1,2,4-trichlorobenzene or hexafluorobenzene, under a pressure of about 0 to about $4.1 \times 10^5$ Pascals (0 to about 60 psi) of an inert gas atmosphere, preferably dinitrogen gas, from about 1 hour to about 96 hours, preferably about 1 hour to about 48 hours. Typically the reaction is carried out in a glass Fisher-Porter bottle equipped with a pressure gauge, internal thermocouple for measuring temperature, and nitrogen gas inlet for pressurizing the apparatus. Alternatively, fullerene compounds of formula II, $(C_{60+2n})R^1{}_mZ_y$, can be reacted with compounds of formula IV, $R^2{}_bCO_2-O_2CR^2{}_b$, such as perfluoroalkanoylperoxide, e.g., $CF_3CF_2CO_2-O_2CCF_2CF_3$, at about 25° to about 100° C. in a halocarbon solvent, such as Freon® 113, under an inert gas atmosphere, such as nitrogen, at 0 to about $4.1 \times 10^5$ Pascals (0 to about 60 psi) from about 1 hour to about 96 hours.

The product from the above reactions is generally isolated by first distilling off all or most of the excess compounds of formula III, $R^2X_q$, and formula IV, $R^2{}_bCO_2-O_2CR^2{}_b$, such as, perfluoroalkylhalide, perfluoroalkyldihalide, or perfluoroalkanoylperoxide; iodine; and any solvent under reduced pressure. The product is dissolved in a halocarbon such as Freon® 113, $CClF_2CCl_2F$, or hexafluorobenzene and filtered. An organic or halocarbon solvent in which the product is not soluble is added to the filtrate, and the product is isolated by decantation of the supernatant, or collecting the product by filtration, after which it is dried. Alternatively, the halocarbon may be removed under reduced pressure to yield the product, which is washed with an organic solvent and then dried.

Mixtures comprising fluoroalkylated fullerene compounds, preferably perfluoroalkylated fullerene compounds, of this invention are useful as lubricants or as additives to lubricants in fluorocarbon- and/or chlorofluorocarbon-based cooling systems, adhesives for fluorocarbon-based polymers, water and corrosion-resistant coatings, gas separation membranes, additives to fluorocarbon polymers and fluoroelastomers for modification of physical properties, and additives to fluorocarbon polymerization reactions.

Unlike most fullerenes known in the art, the mixtures of this invention are surprisingly soluble in a variety of organic liquids, particularly halocarbon liquids, such as chlorofluorocarbons, e.g., $CClF_2CCl_2F$, and hexafluorobenzene.

EXAMPLE 1

A Fisher-Porter tube was charged with 15 mL of 1,2,4-trichlorobenzene (dried over $P_2O_5$, distilled, and stored under nitrogen), 6.00 mL of perfluorohexyliodide (dried over $P_2O_5$, distilled, and stored under nitrogen), and 0.300 g of $C_{60}$. The tube was attached to a stainless steel pressure head equipped with a pressure gauge, and a stainless steel enclosed thermocouple which extended down into the reaction mixture. The apparatus was placed in an oil bath maintained at 200° C. The apparatus developed a pressure of approximately $1.4 \times 10^5$ Pascals (20 psi), and the temperature of the reaction mixture was 175° C. After 24 hours, the reaction was cooled to room temperature, vented to the air, and the reaction mixture was transferred to a flask, using hexafluorobenzene to rinse the reaction apparatus. This rinsing was combined with rest of the reaction mixture in the flask, and the hexafluorobenzene and 1,2,4-trichlorobenzene was distilled off under reduced pressure ($10^{-4} - 10^{-5}$ mm Hg). The dried residue was dissolved in hexafluorobenzene, and this solution was filtered. Hexafluorobenzene was removed in vacuo. The product was then dissolved in 10–20 mL of Freon® 113, and was precipitated by addition of a minimum of dichloromethane. The nearly colorless supernatant was decanted from the oily solid. The dissolution in Freon® 113 and precipitation with dichloromethane was repeated one more time. The product was then dried in vacuo forming a glassy brown solid which was easily broken up with a spatula. Yield: 1.35 g. Elemental Analysis, $^1H$, $^{13}C$, $^{19}F$ Nuclear Magnetic Resonance spectroscopy and negative ion chemical ionization mass spectroscopy indicated the formation of $C_{60}[(CF_2)_5CF_3]_bH_yCl_w$ with an average b of 9, an average y of 2, and an average w of 0.5.

It was not clear if the Cl identified in the analysis as being present on an average of 0.5 was part of residual solvent that was not entirely removed, or if it was attached to the resultant fluoroalkylated fullerene compounds.

EXAMPLE 2

0.4 mL of a saturated benzene solution of $C_{60}$ (~0.002M) in a $4 \times 5$ mm quartz tube was degassed by freeze-pump-thaw cycling on a vacuum system. 500 mL of trifluoromethyl iodide at $1.3 \times 10^3$ Pascals (10 Torr) pressure (~400 equivalents) was condensed into the tube by cooling the latter with liquid nitrogen. The sealed tube was shaken and irradiated at 25° C. in an ultraviolet photoreactor for 30 min. Negative ion chemical ionization mass spectrometry of the dark red solution indicated the formation of $C_{60}(CF_3)_bH_y$ with b=1 to 13 and y=0 to 15. The distribution of products peaked at b=6 and y=4.

EXAMPLE 3

To a glass tube attached to a vacuum system containing 3 mg of $C_{60}$, 1.75 mL of hexafluorobenzene, a drop of mercury, and a small magnetic stirring bar were added 500 mL of trifluoromethyl iodide at $5.3 \times 10^3$ Pascals (40 Torr) pressure (~260 equivalents). The sealed tube was kept in an oil bath at 200° C. with magnetic stirring for 24 hours. Negative ion chemical ionization mass spectrometry revealed the formation of $C_{60}(CF_3)_b$ with b=1 to 14.

EXAMPLE 4

In a nitrogen glove box, 3.5 mL of ~6% by weight diperfluoropropionyl peroxide, $[CF_3CF_2CO_2-]_2$, in Freon® 113 were added to 10 mg of $C_{60}$ (~90 $CF_3CF_2$ groups for each $C_{60}$) in a vial with a magnetic stirring bar. The vial was tightly capped and the contents were stirred at room temperature for two days. Pumping away all volatiles under high vacuum yielded 45 mg of a dark brown powder. Negative ion chemical ionization mass spectrometry indicated the formation of $C_{60}(CF_2CF_3)_b$ with b=5 to 16. The distribution of products peaked at b=12 and 13.

What is claimed is:

1. A process for the preparation of a mixture of fluoroalkylated fullerene compounds comprising: heating fullerene compounds of formula II $$(C_{60+2n})R^1{}_mZ_y \tag{II}$$

wherein n is an integer from 0 to about 470;

$R^1$ is a branched or straight chain hydrocarbon or aromatic hydrocarbon of from 1 to about 100 carbon atoms;

m is an integer of 0 to about 24+n,

Z is independently one or more selected from H, F and Cl;

y is an integer from 0 to about 35+n;

with compounds of formula III $$R^2X_q \tag{III}$$

wherein

R² is a branched or straight chain fluoroalkyl group of from 1 to about 100 carbon atoms;

X is independently Cl, Br or I; and q is an integer of 1 or 2, at a temperature of from about 160° to 300° C., under a pressure of 0 to about $4.1 \times 10^5$ Pascals (0 to about 60 psi) of an inert gas atmosphere, for about 1 hour to about 96 hours; to yield a mixture of fluoroalkylated fullerene compounds comprising formula I $$(C_{60+2n})R^1{}_m R^2{}_b Z_y \qquad (I)$$

wherein b is an integer from 1 to about 24+n.

2. The process of claim 1, further comprising the steps of isolating the fluoroalkylated fullerene compounds by distilling off excess compounds of formula III and any halocarbon solvent under reduced pressure;

dissolving the fluoroalkylated fullerene compounds in a halocarbon;

filtering the fluoroalkylated fullerene compounds;

adding to the filtrate an organic or halocarbon solvent in which the fluoroalkylated fullerene compounds are not soluble; and isolating the fluoroalkylated fullerene compounds by decantation of the supernatant, or collecting the fluoroalkylated fullerene compounds by filtration.

3. The process of claim 1, further comprising the steps of isolating the fluoroalkylated fullerene compounds by distilling off excess compounds of formula III and any halocarbon solvent under reduced pressure;

dissolving the fluoroalkylated fullerene compounds in a halocarbon;

removing the halocarbon under reduced pressure to yield the fluoroalkylated fullerene compounds; and washing the fluoroalkylated fullerene compounds with an organic solvent.

4. The process of claim 1 wherein the temperature is from about 180° to about 200° C., the inert atmosphere is dinitrogen gas and the reaction is carried out in about 1 hour to about 48 hours.

5. The process of claim 1 wherein the compound of formula III is perfluoroalkyliodide or perfluoroalkyldiiodide.

6. The process of claim 5 wherein the perfluoroalkyliodide or perfluoroalkyldiiodide is perfluorohexyliodide, trifluoromethyliodide or I$(CF_2)_4$I.

* * * * *